(12) United States Patent
Goode et al.

(10) Patent No.: US 11,234,753 B2
(45) Date of Patent: Feb. 1, 2022

(54) FLOW BLOCKING ELECTRODE (71) Applicant: Smith & Nephew, Inc., Memphis, TN (US)

(72) Inventors: Johnson E. Goode, Austin, TX (US); Kyle Alan Kapchinski, Austin, TX (US); Melissa Trott Davis, Austin, TX (US)

(73) Assignee: SMITH & NEPHEW, INC., Memphis, TN (US)

( * ) Notice: Subject to any disclaimer, the term of this patent is extended or adjusted under 35 U.S.C. 154(b) by 599 days.

(21) Appl. No.: 15/759,121

(22) PCT Filed: Aug. 16, 2016

(86) PCT No.: PCT/US2016/047196
§ 371 (c)(1),
(2) Date: Mar. 9, 2018

(87) PCT Pub. No.: WO2017/034863
PCT Pub. Date: Mar. 2, 2017

(65) Prior Publication Data
US 2018/0280074 A1 Oct. 4, 2018

Related U.S. Application Data

(60) Provisional application No. 62/209,121, filed on Aug. 24, 2015.

(51) Int. Cl.
*A61B 18/14* (2006.01)
*A61B 18/04* (2006.01)
*A61B 18/00* (2006.01)

(52) U.S. Cl.
CPC ........ *A61B 18/1402* (2013.01); *A61B 18/042* (2013.01); *A61B 18/14* (2013.01);
(Continued)

(58) Field of Classification Search
CPC ... A61B 18/1402; A61B 18/14; A61B 18/042; A61B 18/1482; A61B 2018/00184; A61B 2018/00583; A61B 2218/007
See application file for complete search history.

(56) References Cited

U.S. PATENT DOCUMENTS 4,682,596 A * 7/1987 Bales ................. A61B 18/1492
606/39
4,832,048 A * 5/1989 Cohen ................ A61B 18/1492
600/374

(Continued)

FOREIGN PATENT DOCUMENTS

EP 0547772 A1 11/1992
WO 03028542 A2 4/2003

OTHER PUBLICATIONS

JP Office Action for App No. 2018-510435 dated Apr. 24, 2020, 7 pages.

(Continued)

*Primary Examiner* — Jaymi E Della (57) ABSTRACT

An electrosurgical wand is disclosed. The electrosurgical wand includes a handle that defines a proximal end of the electrosurgical wand. The electrosurgical wand includes an elongate shaft coupled to the handle; the elongate shaft defines a suction lumen therein. The electrosurgical wand also includes an electrically insulative spacer (404) coupled to the distal end of the elongate shaft, whereby the spacer defines a suction channel (412) fluidly coupled to the suction lumen. The electrosurgical wand includes a first means for blocking defined by the spacer, an active electrode (402) coupled on the distal end of the spacer and a second means for blocking associated with the active electrode and in operational relationship to the first means for blocking. In the electrosurgical wand, the first means for blocking includes an annular trough (416) that fully encircles the (Continued)

suction channel of the spacer and the second means for blocking includes an annular wall (414).

8 Claims, 10 Drawing Sheets

(52) U.S. Cl.
CPC .............................. *A61B 18/1482* (2013.01); *A61B 2018/00184* (2013.01); *A61B 2018/00583* (2013.01); *A61B 2218/007* (2013.01)

(56) References Cited

U.S. PATENT DOCUMENTS

| | | |
|---|---|---|
| 5,545,161 A | 8/1996 | Imran |
| 6,623,437 B2 * | 9/2003 | Hinchliffe ............... A61B 10/04 600/564 |
| 2002/0049438 A1 * | 4/2002 | Sharkey ............. A61B 18/1402 606/41 |
| 2006/0259025 A1 | 11/2006 | Dahla |
| 2006/0259031 A1 | 11/2006 | Carmel et al. |
| 2014/0257277 A1 * | 9/2014 | Woloszko ............. A61B 18/14 606/41 |

OTHER PUBLICATIONS

CN Office Action for App No. 201680049002.7 dated Mar. 25, 2020, 11 pages.
Search Report for CN App No. 201680049002.7 dated Mar. 17, 2020, 3 pages.
Office Action for CN App No. 201680049002.7 dated Mar. 25, 2020, 11 pages.
European Patent Office, Office Action in corresponding European application (16756912.8), dated Sep. 4, 2019; 6 pages.
CN OA for o. 201680049002.7 dated Oct. 21, 2020, 11 pages.

* cited by examiner

FLOW BLOCKING ELECTRODE

CROSS-REFERENCE TO RELATED APPLICATIONS

This application claims the benefit of U.S. Provisional Application No. 62/209,121 titled "Flow Blocking Electrode," filed Aug. 24, 2015. The provisional application is incorporated by reference herein as if reproduced in full below.

BACKGROUND

Electrosurgical systems are used by physicians to perform specific functions during surgical procedures. In the realm of arthroscopic surgery, a family of devices is available to aid in removal of tissue based on plasma ablation. Creating and maintaining plasma is a complicated endeavor that involves not only providing the proper conductive fluid proximate to an active electrode, but also controlling flow of the fluid to provide a stable plasma layer for ablative purposes.

SUMMARY

An electrosurgical wand is disclosed including a handle that defines a proximal end of the electrosurgical wand; an elongate shaft coupled to the handle, the elongate shaft defines a suction lumen therein, and a spacer coupled on the distal end of the elongate shaft, the spacer defines a suction channel fluidly coupled to the suction lumen, and the spacer is electrically insulative. The electrosurgical wand further comprises a first means for blocking defined by the spacer, an active electrode coupled on the distal end of the spacer, where an edge of the active electrode aligns with an edge of the spacer. The electrosurgical wand further comprises a second means for blocking associated with the active electrode and in operational relationship to the first means for blocking.

A method is disclosed including generating a plasma proximate to an active electrode disposed on a distal end of an elongate shaft of an electrosurgical wand, the active electrode mates with a spacer coupled on the distal end of the elongate shaft. The method further includes ablating tissue proximate to the active electrode, suctioning portions of fluid proximate to the active electrode through a suction lumen defined within the elongate shaft, and blocking a flow of fluid between the active electrode and the spacer.

An electrosurgical system is disclosed including an electrosurgical wand including a handle that defines a proximal end of the electrosurgical wand, and an elongate shaft coupled to the handle, the elongate shaft defines a suction lumen therein. The electrosurgical system further includes a spacer coupled on the distal end of the elongate shaft; the spacer defines a suction channel fluidly coupled to the suction lumen, and the spacer electrically insulative.

The electrosurgical system further includes an active electrode coupled on the distal end of the spacer, where an edge of the active electrode aligns with an edge of the spacer and a means for blocking flow between a back side of the active electrode and the spacer. The electrosurgical system further includes an electrosurgical controller electrically coupled to the electrosurgical wand, the electrosurgical controller including a processor, a memory coupled to the processor, and an electrical generator operatively coupled to the processor, the electrical generator defines an active terminal coupled to the active electrode, and the electrical generator defines a return terminal. The memory in the electrosurgical system stores a program that, when executed by the processor causes the processor to generate a plasma proximate to the active electrode, and suction portions of fluid proximate to the active electrode by way of the suction lumen.

BRIEF DESCRIPTION OF THE DRAWINGS

For a detailed description of exemplary embodiments, reference will now be made to the accompanying drawings in which:

FIG. 4c shows a cross-sectional view of an electrosurgical wand taken along line 4C-4C of FIG. 4a;

FIG. 6b shows a cross-sectional view of an electrosurgical wand taken along line 6B-6B of FIG. 6a;

NOTATION AND NOMENCLATURE

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Ablation" shall mean removal of tissue based on tissue interaction with a plasma.

"Active electrode" shall mean an electrode of an electrosurgical wand which produces an electrically-induced tissue-altering effect when brought into contact with, or close proximity to, a tissue targeted for treatment.

"Blocking" shall mean reducing a flow of liquid and does not require a complete disruption to the flow of liquid.

"Aligns" as between an electrode and a spacer shall mean that an edge of the electrode exactly aligns or the electrode is within manufacturing tolerance of the edge of the spacer without overhang, i.e., the electrode does not hang over the edge of the spacer.

A fluid conduit said to be "within" an elongate shaft shall include not only a separate fluid conduit that physically resides within a internal volume of the elongate shaft, but also situations where the internal volume of the elongate shaft is itself the fluid conduit.

Where a range of values is provided, it is understood that every intervening value, between the upper and lower limit of that range and any other stated or intervening value in that state range is encompassed within the invention. Also, it is contemplated that any optional feature variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The references items are provided solely for their disclosure prior to the filing date of the present application. Nothing herein is to be construed as an admission that the present invention is not entitled to antedate such material by virtue of prior invention.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Thus, it is to be understood that this invention is not limited to particular variations set forth herein as various changes or modification may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The various embodiments are directed to electrosurgical methods and related electrosurgical systems. The electrosurgical system may apply electrical energy to a target location by way of an electrosurgical wand. The electrosurgical system may be used in procedures where a site is flooded or submerged with an electrically conducting fluid, such as arthroscopic surgery of the knee, shoulder, ankle, hip, elbow, hand, or foot. In other procedures, the various embodiments may be useful for collagen shrinkage, ablation, and/or hemostasis in procedures for treating target tissue alone or in combination with the volumetric removal of tissue. In particular, the various embodiments are directed to an electrosurgical system having an electrosurgical wand with a means to block a flow of liquid along the side of the tip of the wand. In example embodiments, the means for blocking, blocks the flow of liquid between an active electrode at the tip of the wand and a spacer disposed adjacent to the active electrode. The specification first turns to an illustrative system to orient the reader.

Figure 1:
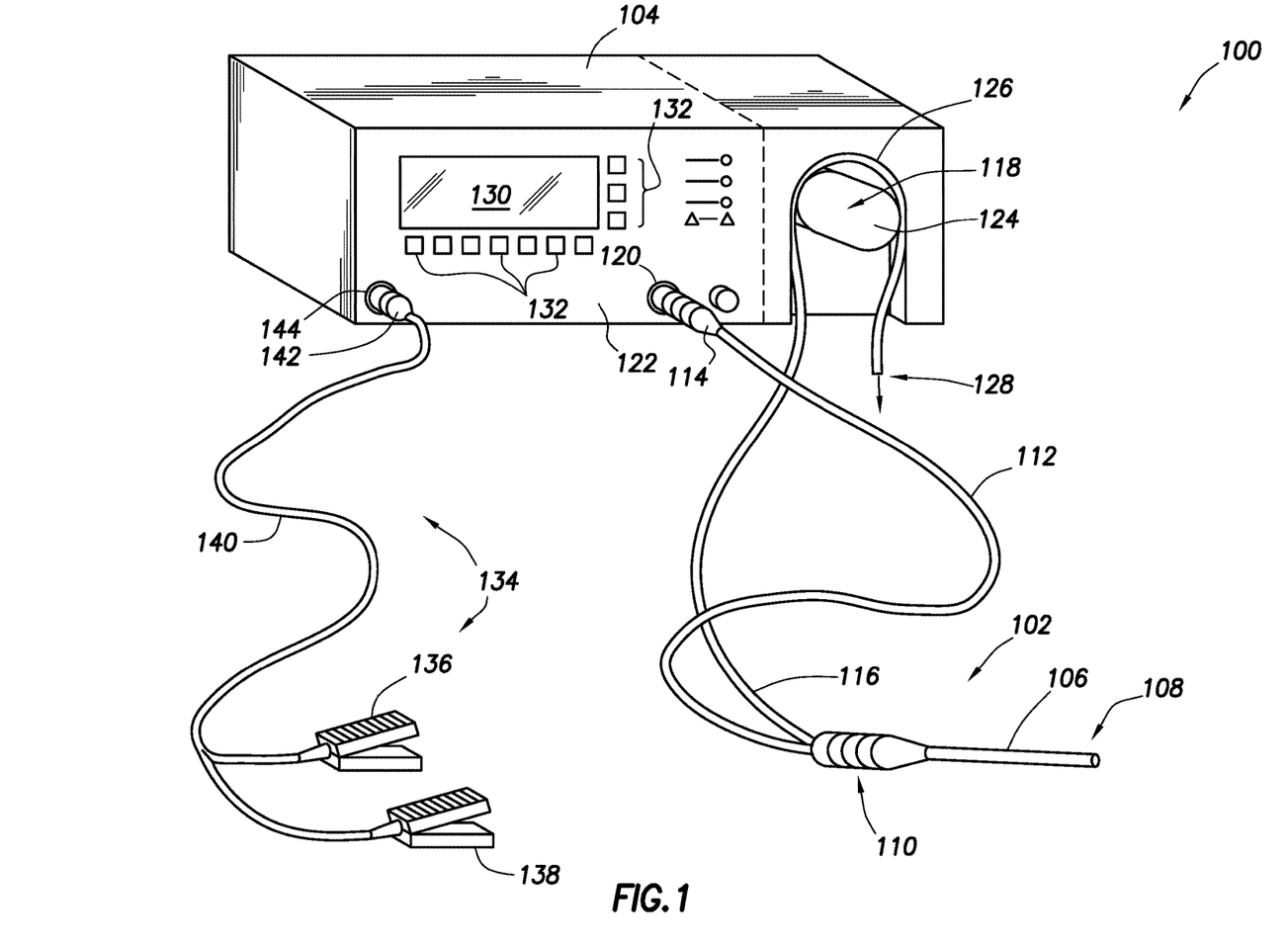
FIG. 1 shows an electrosurgical system in accordance with at least some embodiments.

FIG. 1 illustrates an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate shaft 106 that defines distal end 108. The elongate shaft 106 further defines a handle or proximal end 110, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to provide aspiration at the distal end 108 of the wand. In accordance with various embodiments, the tubular member 116 couples to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lines in the figure), but in any event the peristaltic pump is operatively coupled to the controller 104. In other example systems, the tubular member 116 may couple to any source of vacuum, such as a vacuum source available in a hospital and/or surgical centers.

The example peristaltic pump 118 comprises a rotor portion 124 (hereafter just "rotor 124") as well as a stator portion 126 (hereafter just "stator 126"). The flexible tubular member 116 couples within the peristaltic pump 118 between the rotor 124 and the stator 126, and movement of the rotor 124 against the flexible tubular member 116 causes fluid movement toward the discharge 128. While the illustrative peristaltic pump 118 is shown with a two-head rotor 124, varying types of peristaltic pumps 118 may be used (e.g., a five-head peristaltic pump). In the context of the various embodiments, the peristaltic pump 118 creates a volume-controlled aspiration from a surgical field at the distal end 108 of the wand 102, with the control based on a speed of the rotor 124, as commanded by the controller 104.

Still referring to FIG. 1, a display device or interface device 130 is visible through the enclosure 122 of the controller 104, and in some embodiments a user may select operational modes of the controller 104 by way of the interface device 130 and related buttons 132. The interface device 130 may also be the location where information is provided to an operator such as a surgeon. For example, the interface device 130 may display an indication that the active electrode of the wand 102 is approaching, has reached, or has exceeded the useful life.

In some embodiments, the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller may comprise a corresponding connector 144 that couples to the pedal connector 142. An operator may use the foot pedal assembly 134 to control various aspects of the controller 104, such as the mode of ablation or aspiration volume created by the peristaltic pump 118. In certain embodiments, control of the various operational or performance aspects of controller 104 may be activated by selectively depressing finger buttons located on handle 110 of wand 102 (finger buttons not specifically shown so as not to unduly complicate the figure).

The electrosurgical system 100 of the various embodiments may have a variety of operational modes. One such mode employs Coblation® technology. In particular, the assignee of the present disclosure is the owner of Coblation® technology. Coblation® technology involves the application of RF energy between one or more active electrodes and one or more return electrodes of the wand 102 to develop high electric field intensities in the vicinity of the target issue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline.

When the electrically conductive fluid is heated to the point that the atoms of the fluid vaporize faster than the atoms recondense, a vapor or gas is formed. When sufficient energy is applied to the vapor or gas, the atoms collide with each other causing a release of electrons in the process, and an ionized gas or plasma is formed (the so-called "fourth state of matter"). Stated otherwise, plasma may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of plasma becomes sufficiently low (i.e., less than approximately $10^{20}$ atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Some factors may be controlled during operation of the electrosurgical system 100 and other factors may be controlled during manufacturing of the distal end 108.

For example, during operation of the electrosurgical system 100 may be configured to produce energy sufficient to break the molecular bonds of certain tissue but insufficient to break the molecular bonds of other tissue. As an example, fatty tissue (e.g., adipose) has double bonds that require an energy level higher than 4 eV to 5 eV (i.e., on the order of about 8 eV) to break. Accordingly, the Coblation® technology in some modes of operation does not ablate such fatty tissue; however, the Coblation® technology at the lower energy levels may be used to effectively ablate cells to release the inner fat content in a liquid form. Other modes of operation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120, and 6,296,136, the complete disclosures of which are incorporated herein by reference.

Factors that may be controlled at the design and manufacturing stage of the distal end 108 may include designing the distal end 108 such that during operation of the electrosurgical system 100, a path of fluid is controlled along the distal end 108. A shape and design of the distal end 108 may impact the overall performance of the electrosurgical system 100. For example, in some designs, an electrode purposed for the creation of plasma on the distal end 108 is attached to an insulating material (insulator) where a gap exists between the electrode and insulator. This gap occurs due to manufacturing limitations or as a side effect of manufacturing limitations. When the electrosurgical system 100 has suction incorporated into the function of the device, the gap between the electrode and the insulator can prevent the formation and ability to maintain a plasma layer on a tissue treating surface of the active electrode because additional flow under and across the sides of the electrode can affect the conditions that are preferential for plasma to form. Controlling or limiting the fluid flow may more optimally control where the vapor layer forms on the active electrode and thereby where the plasma may form and treat tissue. Fluid that flows to areas that do not treat tissue may reduce the efficiency of plasma formation, make plasma formation more difficult to control and potentially cause instrument degradation. Additionally, the undesired flow under the sides of the electrodes can reduce the flow through one or more lumens on the face of the electrode that are specifically purposed for suction.

Figure 2:
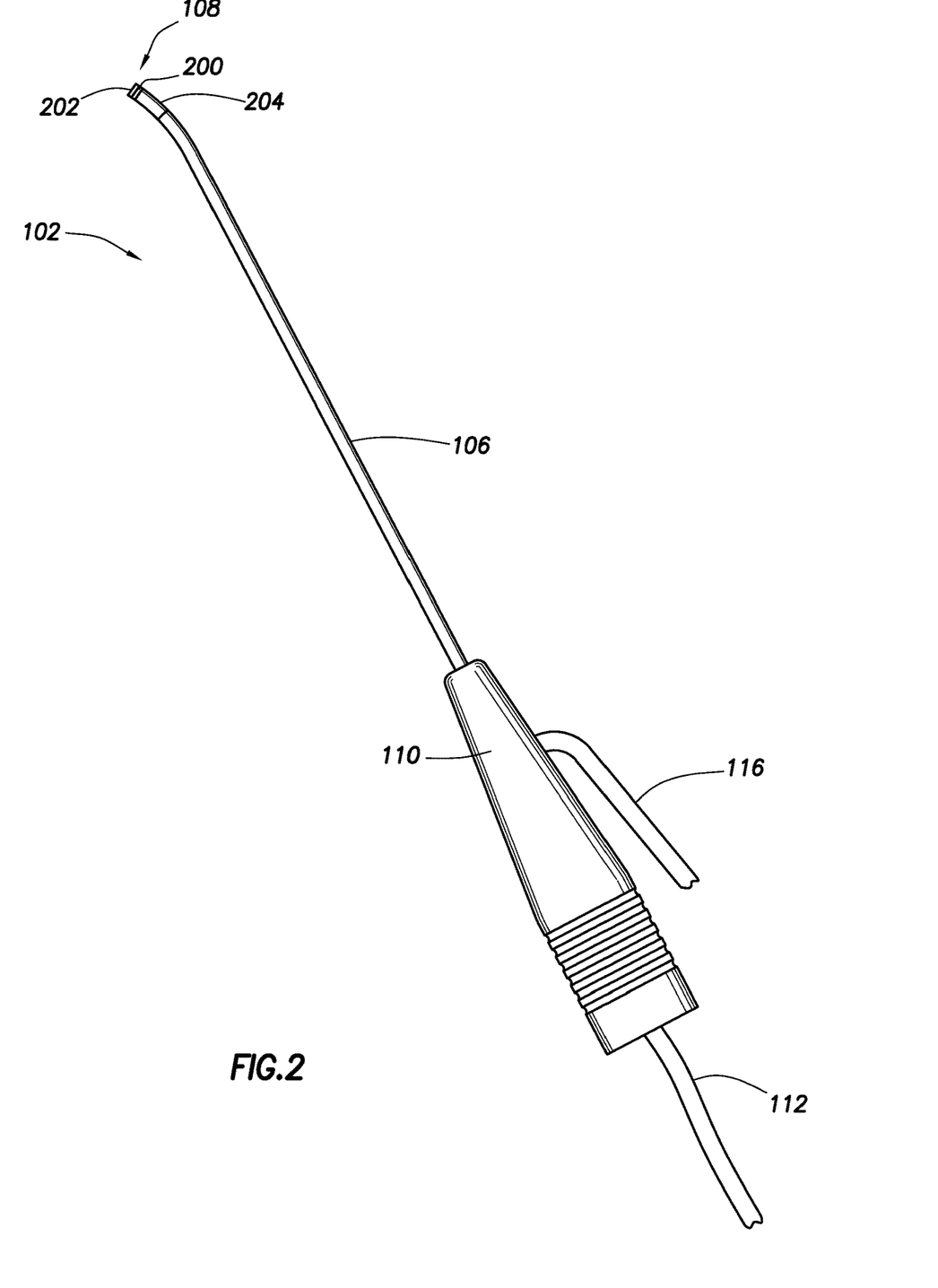
FIG. 2 shows an elevation view of an electrosurgical wand in accordance with at least some embodiments.

FIG. 2 shows an elevation view of wand 102 in accordance with example systems. In particular, wand 102 comprises elongate shaft 106 which may be flexible or rigid, a handle 110 coupled to the proximal end of the elongate shaft 106, and an insulator or spacer 200 coupled to the distal end of elongate shaft 106. Also visible in FIG. 2 is the flexible tubular member 116 extending from the wand 102 and the multi-conductor cable 112. The wand 102 comprises an active electrode 202 disposed on the distal end 108 of the elongate shaft 106. Active electrode 202 may be coupled to an active or passive control network within controller 104 (FIG. 1) by means of one or more insulated electrical connectors in the multi-conductor cable 112. The active electrode 202 is electrically isolated from a common or return electrode 204 which is disposed on the shaft proximal of the active electrode 202.

The spacer 200 is positioned distal to the return electrode 204 and may be composed of an electrically insulating and plasma resistant material such as epoxy, plastic, ceramic, silicone, glass, or the like. Spacer 200 extends from the distal end 108 of elongate shaft 106 (usually about 1 to 20 mm) and provides support for active electrode 202. Although attempts are made to dispose the active electrode 202 as close as possible to the spacer 200, due to manufacturing limitations, a gap may be present between the two. As discussed previously, this gap may introduce an undesirable flow between the electrode 202 and spacer 200. During operation of the electrosurgical system 100, fluid comprising ablated tissue may be suctioned through one or more suction lumen on the face of the electrode 202.

Figure 3:
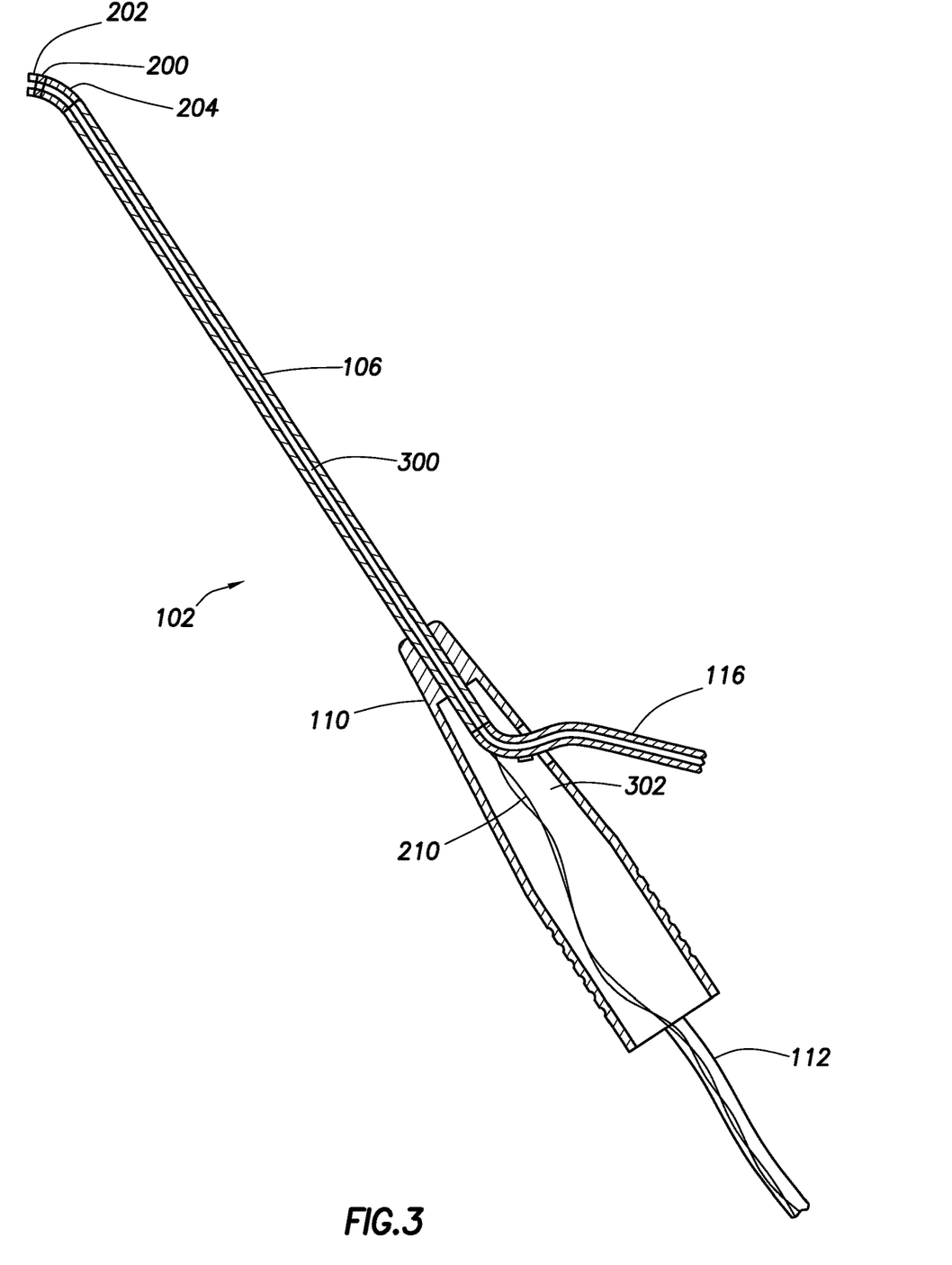
FIG. 3 shows a cross-sectional elevation view of an electrosurgical wand in accordance with at least some embodiments.

FIG. 3 shows a cross-sectional elevation view of the wand 102 in accordance with example embodiments. In particular, wand 102 comprises a suction lumen 300 defined within the elongate shaft 106. In the example wand 102 of FIG. 3, the inside diameter of the elongate shaft 106 defines the suction lumen 300, but in other cases a separate tubing within the elongate shaft 106 may define the suction lumen 300. The suction lumen 300 may be used for aspirating excess fluids, bubbles, tissue fragments, and/or products of ablation from the target site through one or more apertures in or around the active electrode 202. Suction lumen 300 extends into the handle 110 and fluidly couples to the flexible tubular member 116 for coupling to the peristaltic pump 118 (FIG. 1) or other source of aspiration suction.

Handle 110 also defines an inner cavity 302 within which electrical conductors 210 may reside, where the electrical conductors 210 may extend into the multi-conductor cable 112 and ultimately couple to the controller 104 (FIG. 1). The electrical conductors 210 likewise extend through the elongate shaft and couple, one each, to the return electrode 204 and the active electrode 202.

When an active electrode 202 purposed for the creation of plasma on an RF plasma medical device (such as the wand 102) is attached to an insulating material (such as a spacer 200), a gap can exist between the electrode and the spacer. A flat screen electrode of a metal injection molded (MIM) or machined electrode may have a gap with the spacer due to the tolerances associated with machining or sintering the electrode. As previously mentioned, this gap may result in undesirable flow of fluid under and across the sides of the electrode, which affects conditions preferential for plasma formation as well as an overall performance of the device.

To prevent undesired flow under and across the sides of the electrode, two different design methods have been used in the related art devices. First, the mating fit of contact surfaces between the electrode and insulator is designed and manufactured to be a very close fit. The close fit mating between the electrode and the insulator will reduce the flow under the electrode. The close fit is possible with some manufacturing methods, but the very close fit mating to achieve desired performance cannot easily be achieved with some machined and molded designs of electrodes and insulators, and extra expense and secondary processes on the components may be required to achieve a close fit. In a second related art design, the electrode has been inset into the insulator/spacer so that the flow cannot pass under the electrode as easily. An example of an inset electrode is shown in patent application US20090048592. Setting the electrode into the insulator limits the ability of the surface and edges of the electrode to contact tissue. Tissue contact with the electrode is desirable to aid in breaking down tissue when plasma is present on the electrode.

Figure 4A:
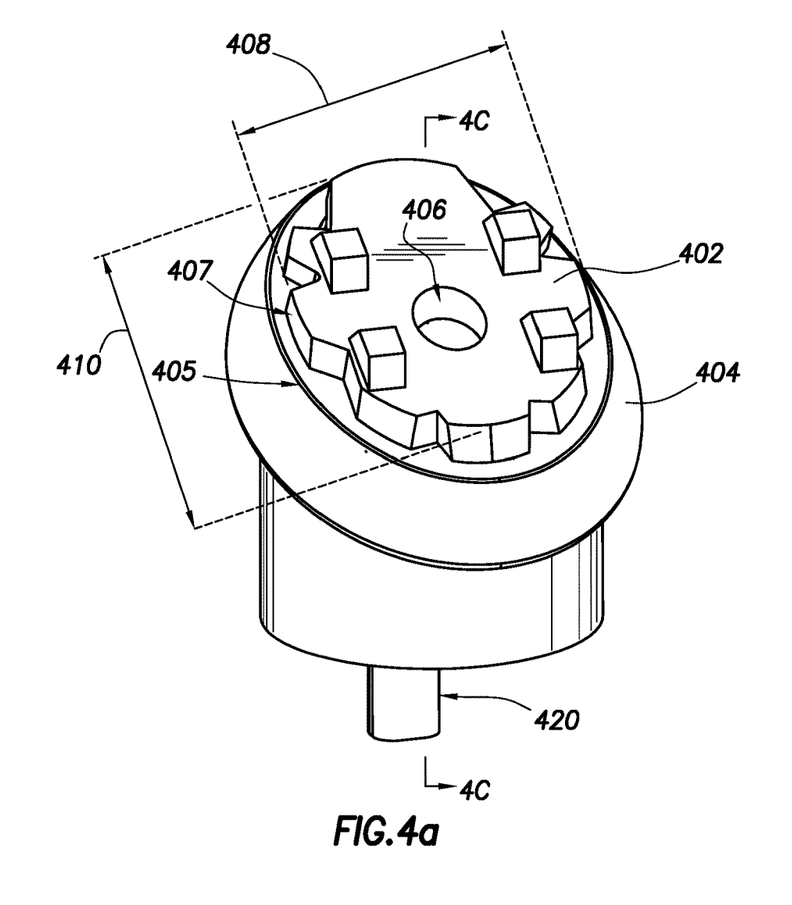
FIG. 4a shows a view of a distal end of an electrosurgical wand.

FIG. 4a shows a view of a combined electrode and insulator in accordance with example systems. In particular, FIG. 4a shows insulator 404 and perched on the distal tip of the insulator 404 is an active electrode 402. Unlike the design method in which an electrode may be inset into or sunk into an insulator/spacer, the combined electrode and insulator in FIG. 4a comprises an active electrode and insulator with edges that align. That is, in FIG. 4a, a substantial portion of the outer edge 407 of the active electrode 402 aligns with the outer edge 405 of a distal surface of the insulator 404. As shown in FIG. 4a the active electrode edges 407 are slightly set back, however this is predominantly so as to compensate for manufacturing tolerances. In some cases the outer edge 407 of the active electrode may be slightly set back from the outer edge 405 of the insulator 404 by between 1 and 15 thousandths of an inch so as to compensate for these tolerances while preventing an overhang. This is preferable, as overhang of the active electrode or electrode edges that extend over and beyond an insulator edge is not desired because such overhang tends to snag tissue and pull the active electrode away from the insulator.

As the edge 407 of the active electrode 402 aligns with the edge 405 of the insulator 404, an edge effect may be achieved in which an edge or edge surface of the active electrode 402 may touch tissue during operation of the device (such as the wand 102). The ability of a device such as wand 102 to achieve an edge effect increases the effective performance of the wand 102 and thus a configuration in which an edge 407 of the active electrode 402 aligns with an edge 405 of the insulator 404 may be desirable.

Figure 4B:
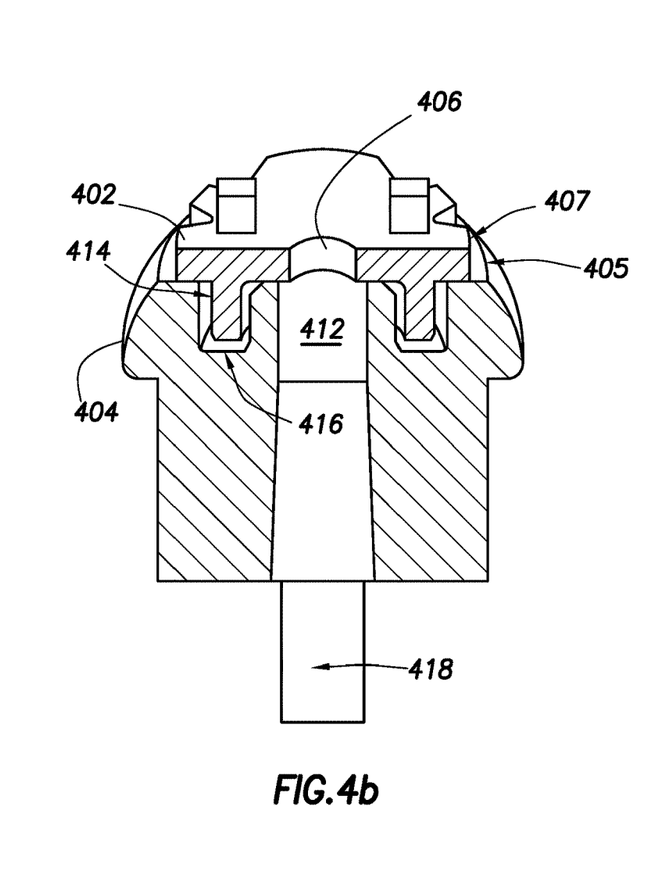
FIG. 4b shows a cross-sectional view of a distal end of an electrosurgical wand.

The active electrode 402 comprises at least one aperture 406 (there may be multiple apertures 406) which resides over a suction channel in the insulator 404 (suction channel 412 shown in FIG. 4b). The active electrode 402 has width as indicated by width indicator 408 between about 60 and 200 thousandths, and a length as indicated by length indicator 410 between about 60 and 200 thousandths. Additionally, an electrical connection 420 is shown depicting an extension of the active electrode through the insulator which connects to electrical conductors 210 (FIG. 3) within an inner cavity of the handle 110 (FIG. 3).

FIG. 4b is a cross-sectional view of the combined electrode and spacer insulator in FIG. 4a, with a cross-sectional cut through the longitudinal axis. Visible in FIG. 4b is the insulator 404, edge 405 of the insulator 404, active electrode 402, edge 407 of the active electrode 402, suction channel or hole 412 defined within the insulator 404, as well as the internal suction lumen 418 disposed within the shaft of the wand. Internal suction lumen 418 may be a separate piece comprising a pipe or tube that is fit into or fluidly coupled with the suction channel 412. In other embodiments, the suction lumen 418 may be defined by a pipe that fits around or telescopes over the bottom of the insulator 404. The aperture 406, suction channel 412 and suction lumen 418 are fluidly coupled to each other. The aperture 406 feeds into the suction channel 412 which feeds into the suction lumen 418.

In accordance with example embodiments, the active electrode 402 is a flow blocking electrode, and as such the flow blocking electrode has a feature on the mating side of the active electrode that interfaces with the insulator/spacer. In FIG. 4b, the flow blocking feature is in the form of a downward protruding wall 414, where the wall extends into an annular trough 416 that fully encircles the suction channel 412. In some embodiments the annular trough may encircle most of but not all of the suction channel 412. The downward protruding wall 414 is radially spaced or offset from both the outer periphery of the active electrode and suction aperture 406. The flow blocking feature creates a tortuous path between the suction channel/suction hole 412 in the insulator 404 and the circumferential outer edges of the active electrode 402 and the insulator 404. The purpose of the tortuous path is to reduce the flow under and across the sides of the active electrode 402 by increasing the resistance to flow from the circumferential peripheral edge of the electrode 402 to the suction channel/suction hole 412 in the insulator 404. The tortuous path acts to reduce bypass flow of fluids between the active electrode 402 and the insulator 404, thus forcing most, if not all of the fluid to flow through the aperture 406 from the tissue contacting the surface of the active electrode 402 and then into the suction channel 412.

The tortuous path reduces the effective suction that pulls fluid into any gaps where the active electrode 402 mates with the insulator and therefore less fluid is drawn through these gaps. The flow blocking feature enables higher device performance for designs where the outer peripheral edge of the active electrode 402 aligns with the insulator 404 by limiting flow across the edge and under the electrode 402. Accordingly, the flow blocking feature improves the performance of a device such as wand 102 where the active electrode 402 extends to the outer circumference of the insulator 404, where the active electrode 402 is able to contact tissue targeted for removal.

Figure 4C:
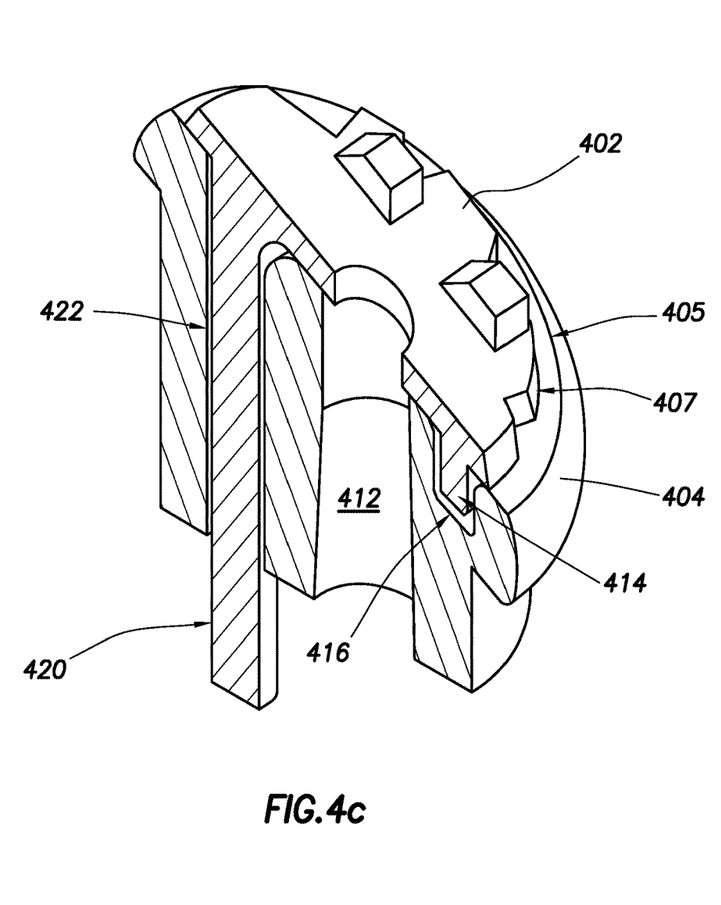

FIG. 4c shows a cross-sectional view taken along line 4C-4C of FIG. 4a. Visible in FIG. 4c is the insulator 404, edge 405 of the insulator, active electrode 402, and edge 407 of the active electrode 402. The suction channel 412 is shown as well as the downward protruding wall 414 and annular trough 416. In addition to having a downward protruding wall 414, the active electrode 402 may also have a portion defining electrical connection 420 that extends further into the insulator 404 than the protruding wall 414. The electrical connection 420 extends through a channel 422 that is separate and apart from the suction channel 412. The bulk of the flow blocking feature (i.e., the combination of the downward protruding wall 414 and the annular trough 416) may not preferably provide any fixation means or an electrical connection between an energy supply and the active electrode 402. Instead, the electrical connection 420 provides the means for an electrical connection through the insulator to the electrical conductors 210 in the handle 110 (FIG. 3).

Figure 5:
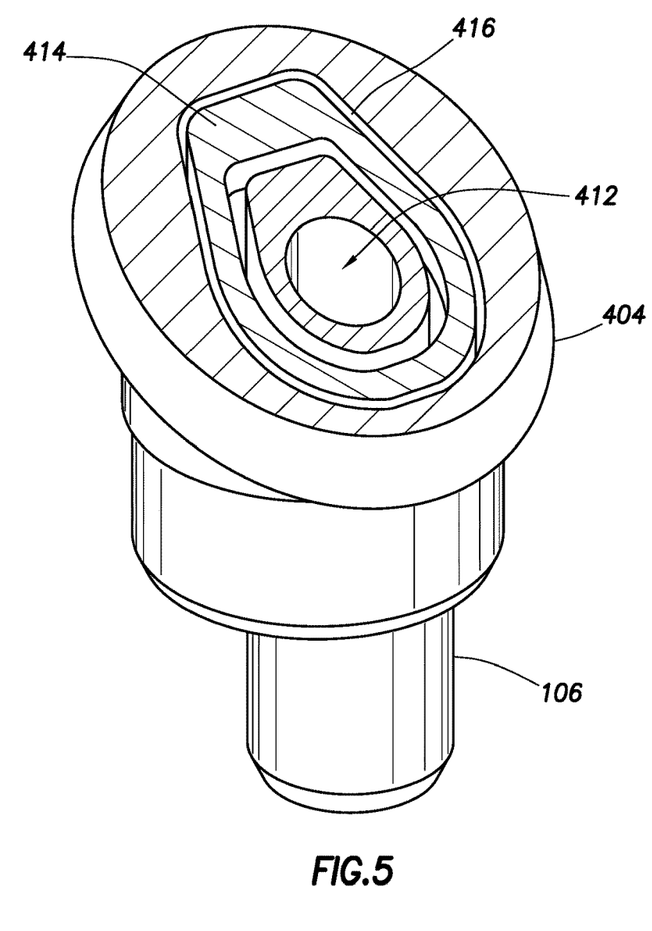
FIG. 5 shows a perspective view of a distal end of an electrosurgical wand with the active electrode partially removed.

FIG. 5 shows a perspective view of the devices of FIGS. 4a-4c, but in this case with the cut along the bottom of the active electrode 402 at the location where the wall 414 extends into the trough 416. Thus, the view is of a distal end of the wand 102 with the active electrode partially removed. In the example embodiment shown in FIG. 5, trough 416 fully encircles the suction channel 412, and likewise the wall 414, extending into the trough 416 fully encircles the suction channel 412. Both the trough 416 and wall 414 may be annular or be placed in any manner that fully or mostly circumscribes the suction channel 412. That is, in some embodiments, the trough 416 or wall 414 may partially circumscribe the suction channel 412.

In example systems, the length or height of the wall 414, measured from the back side of the active electrode, may be 10 to 50 thousandths, and the trough 416 has a depth slightly greater (e.g., 1 to 10 thousandths) than the length of the wall 414. In some embodiments, the length or height of the annular wall 414 is nonzero and less than or equal to half of a width of the active electrode 402. In some embodiments the length or height of the annular wall 414 is nonzero and less than or equal to ⅝th of a width of the active electrode 402.

As discussed, in example systems, the active electrode 402 (FIG. 4) electrically couples to conductors within the wand 102 by having a portion (in view of FIG. 5, the thicker flat portion where the reference number 414 is pointing to) that extends down into the insulator 404 through a channel separate and apart from the suction channel 412. In various embodiments, the bulk of the flow blocker is not intended to provide any fixation means or electrical connection to the spacer/wand. In some cases, the wall 414 extends into the trough 416, and no other materials reside therein. In other cases, the trough 416 may contain an adhesive or filler to help seal against suction flow, and to better hold the active electrode 402 (FIG. 4) against the insulator 404.

Figure 6A:
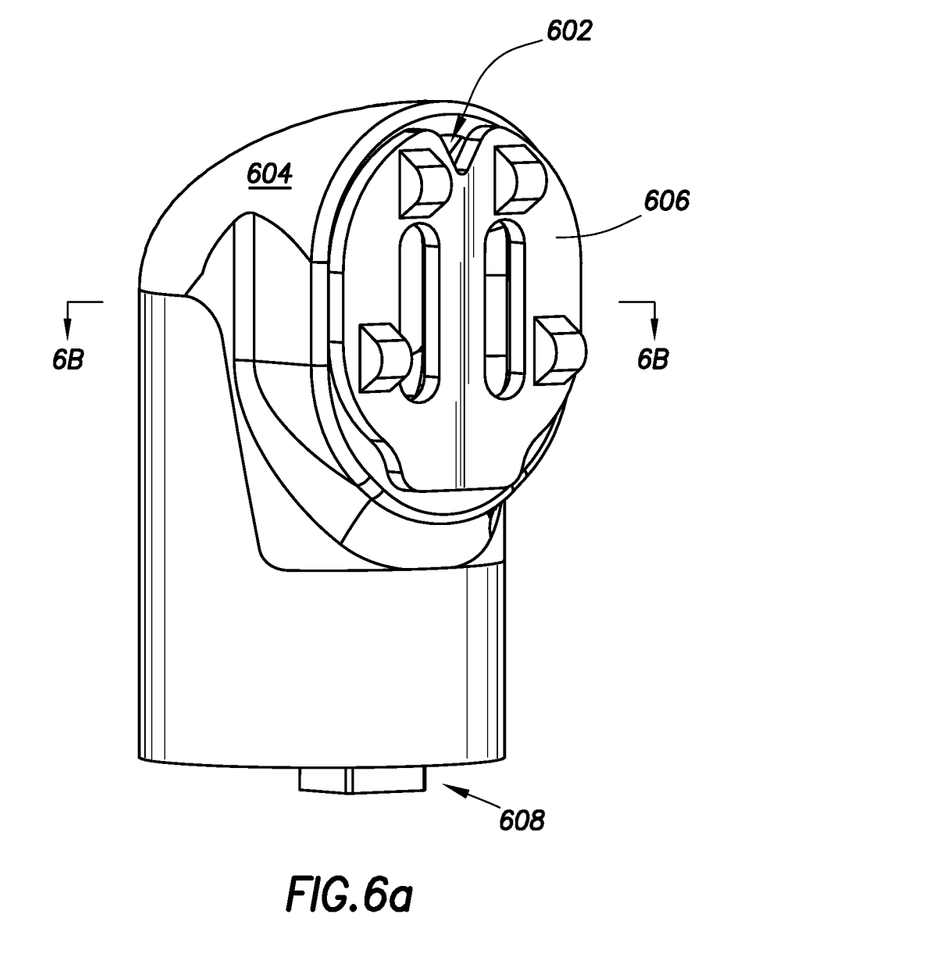
FIG. 6a shows a partial side elevation view of an electrosurgical wand.

FIG. 6a shows a partial side elevation view of another example embodiment of a combined electrode and spacer. In FIG. 6a, a bypass aperture 602 is located on the face of the active electrode 606 near the periphery of the active electrode 606 and is fluidly connected to a suction channel defined within the insulator 604. The active electrode 606 is approximately parallel to the shaft 106 of the wand 102 (FIG. 1). Electrical connection 608 defines a portion of the active electrode 606 that extends through the insulator 604 and provides a means for an electrical connection through the insulator to the electrical conductors 210 in the handle 110 (FIG. 3).

Figure 6B:
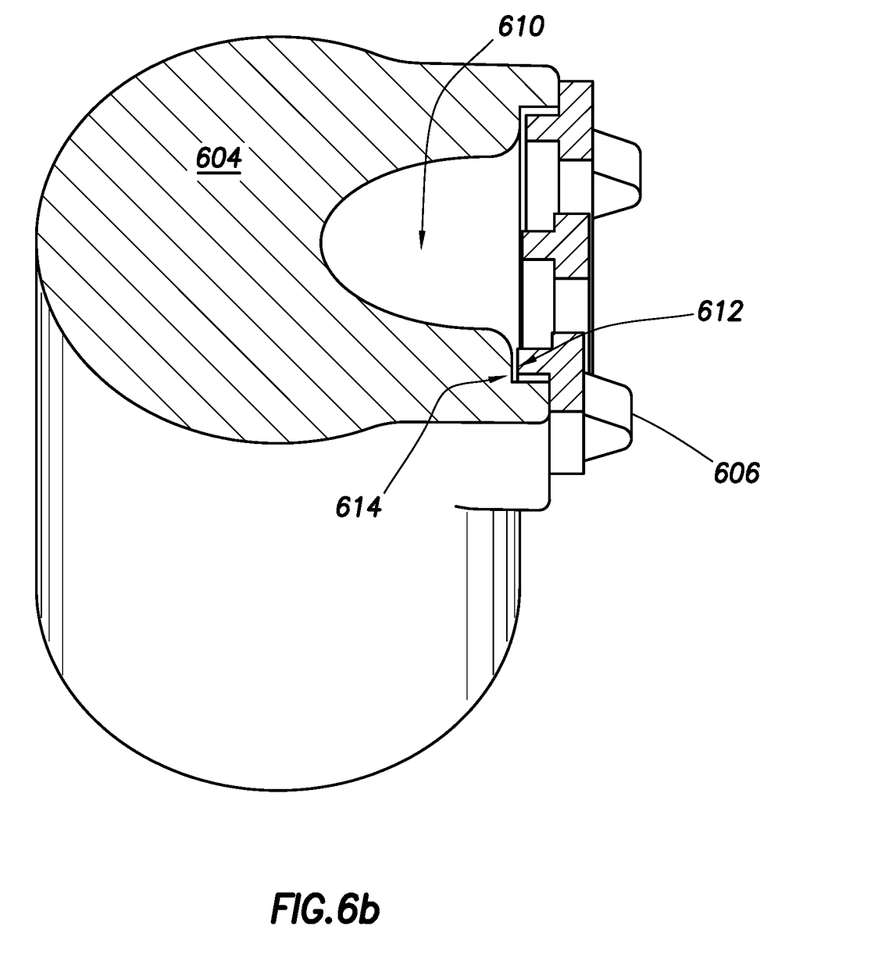

FIG. 6b shows a cross-sectional view taken along line 6B-6B of FIG. 6a. FIG. 6b shows the cross-sectional view of the device with a longitudinal cut along the distal tip and across half the active electrode 606. Suction channel 610 is defined within the insulator 604. A means for blocking fluid is illustrated in this view. In particular, in example systems, the tortuous path is created by a shoulder region 612 of the active electrode 606 fitting into a shoulder region 614 of the insulator 604. Similar to the protruding wall 414, the shoulder region 612 is defined on the back side of the active electrode 606. The shoulder regions 612 and 614 are shaped to mirror each other such that when the active electrode 606 is disposed next to the insulator 604, the shoulder regions 612 and 614 may abut each other. Due to manufacturing tolerances however a small gap may be present. Thus, the creation of the tortuous path is defined by a wall defined on the back side of the active electrode that extends into a trough defined within an abutting insulator, where the trough defines a channel within which the wall fits into. In embodiments comprising shoulder regions 612 and 614 keyed with each, a tortuous path seal may also be formed to reduce or eliminate flow at remaining locations.

Figure 6C:
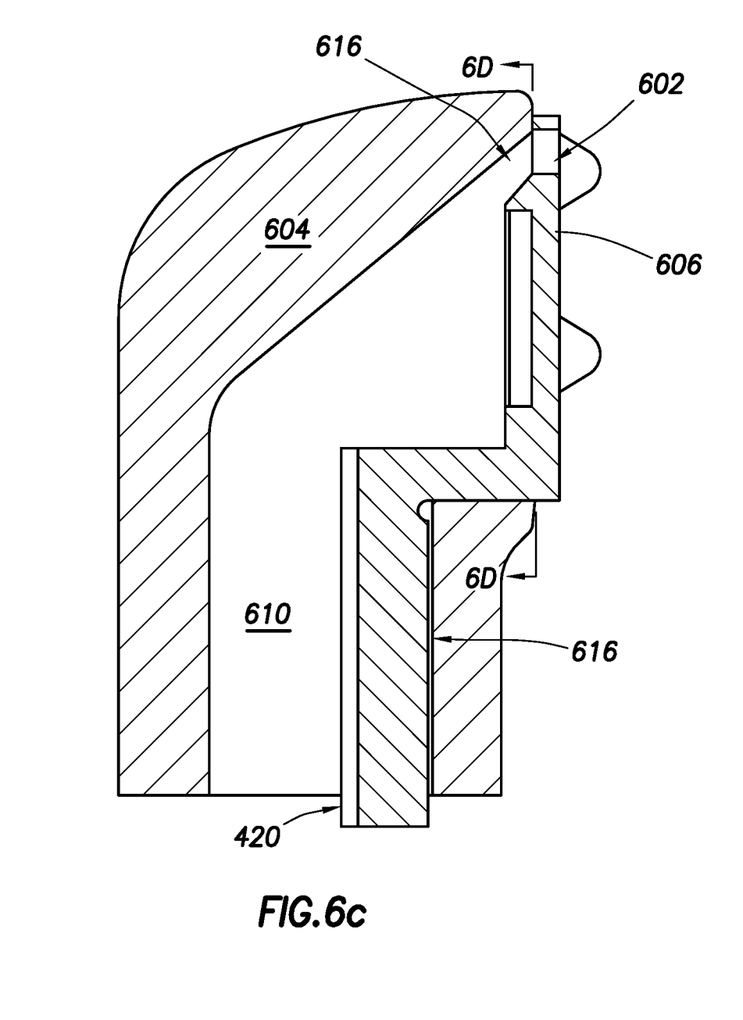
FIG. 6c shows a cross-sectional view of an electrosurgical wand.

FIG. 6c shows a partial cross-sectional view with a latitudinal cut from the face of the active electrode 606 to the distal back of the insulator 604. Bypass aperture 602 is located at the top of the active electrode 606. A pathway for suction 614 may enable bypassing other apertures in the active electrode 606, and is fluidly coupled to suction channel 610. The electrical connection 420 extends from a bottom portion of the active electrode 606, away from the face of the active electrode 606 and into the insulator 604. The active electrode 606 electrically couples to conductors within the wand 102 (FIG. 1) by having the electrical connection 606 extend through the insulator 604 through a channel 616 separate and apart from the suction channel 610. Thus, the bulk of the flow blocker (i.e., the combination of the shoulder regions 612 and 614) is not intended to provide any fixation means or electrical connection to the insulator 604.

Figure 6D:
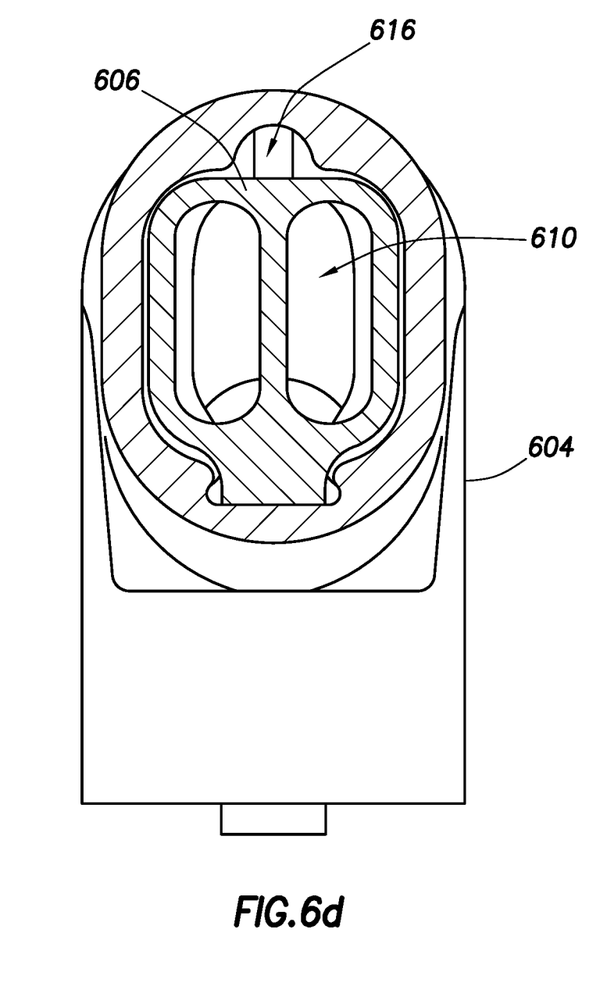
FIG. 6d shows a cross-sectional view of an electrosurgical wand taken along line 6C-6C of FIG. 6c

FIG. 6d shows a cross-sectional view taken along line 6D-6D of FIG. 6c. Thus, FIG. 6d provides a view in which a portion of the active electrode 606 is removed. The remaining portion of the active electrode 606 that is shown, illustrates the placement of the electrode 606 on an insulator 604. Electrode 606 comprises a shoulder region 612 (FIG. 6b) defined on the back side of the active electrode 606 and the shoulder region 612 abuts the shoulder region 614 defined within the top of insulator 604 (FIG. 6b). As discussed, the shoulder regions 612 and 614 (FIG. 6b) mirror each other. Bypass pathway 616 is fluidly couples the bypass aperture 602 (FIGS. 6a and 6b), of the active electrode 606 to the suction channel 610. In some embodiments, the placement of the bypass aperture 602 (FIGS. 6a and 6b) creates an opening in the tortuous path and creates a preferential flow along the topside of the electrode 606 at the location of the bypass aperture 602. Some embodiments may use this configuration due to size constraints. For example, some embodiments, may include the active electrode 606 with a flow blocker implemented on the back side of the active electrode 606 (i.e., shoulder region 612 or a wall 414 (FIG. 4)), but due to size constraints, it may be difficult to create an insulator with a portion that fits inside the flow blocking element.

In various embodiments, an electrode and spacer combination implementing flow blocking capability may include an active electrode with both a protruding wall (such as discussed in FIGS. 4a-4c) as well as a shoulder region (such as discussed in FIGS. 6a-d) defined on the back of the active electrode. Additionally, an insulator corresponding to an electrode with both a protruding wall and shoulder region may include both a trough (such as discussed in FIGS. 4a-4c) as well as a shoulder region that mirrors the shoulder region defined on the back of the active electrode (such as discussed in FIGS. 6a-d). Additionally, in some embodiments, the tortuous path may be present in the active electrode where a portion of the insulator protrudes into a backside of the active electrode. Thus, an embodiment discussed in FIGS. 4a-4c is not exclusive to features that may be present in embodiments discussed in FIGS. 6a-d, and vice versa. That is, the means for implementing flow blocking may be varied and include all features discussed in the figures or partial features of those discussed in the figures.

Generally, this disclosure describes an electrode and supporting insulative spacer, shaped so as to cooperatively form a means of reducing fluid flow underneath the active electrode surface. This means of reducing fluid flow incorporates altering a path any fluid may take as it seeps or ingresses between mating surfaces of the spacer and active electrode. Prior to incorporating means for reducing fluid flow a path between the mating surfaces exists due to innate surface characteristics of the materials used and normal manufacturing processes. A tortuous path introduced between the mating surfaces may begin at the outer circumferential edge or edge surface of the active electrode, progress through the mating surfaces and end at a suction aperture of the electrode or spacer. The tortuous path may begin by extending in a first radial direction relative to an electrode tissue treatment surface. The tortuous path direction may then extend at an angle relative to the first direction, in some embodiments at about a 90 degree angle relative to the first direction and away from the active electrode tissue treatment surface. The tortuous path direction may then further wind between the mating active electrode and spacer and change direction so as to extend in the first radial direction, and may then change direction once more to extend at an angle relative to the first radial direction again. By changing the direction of the fluid flow path so that the path forms a tortuous path, fluid ingress is reduced.

Figure 7:
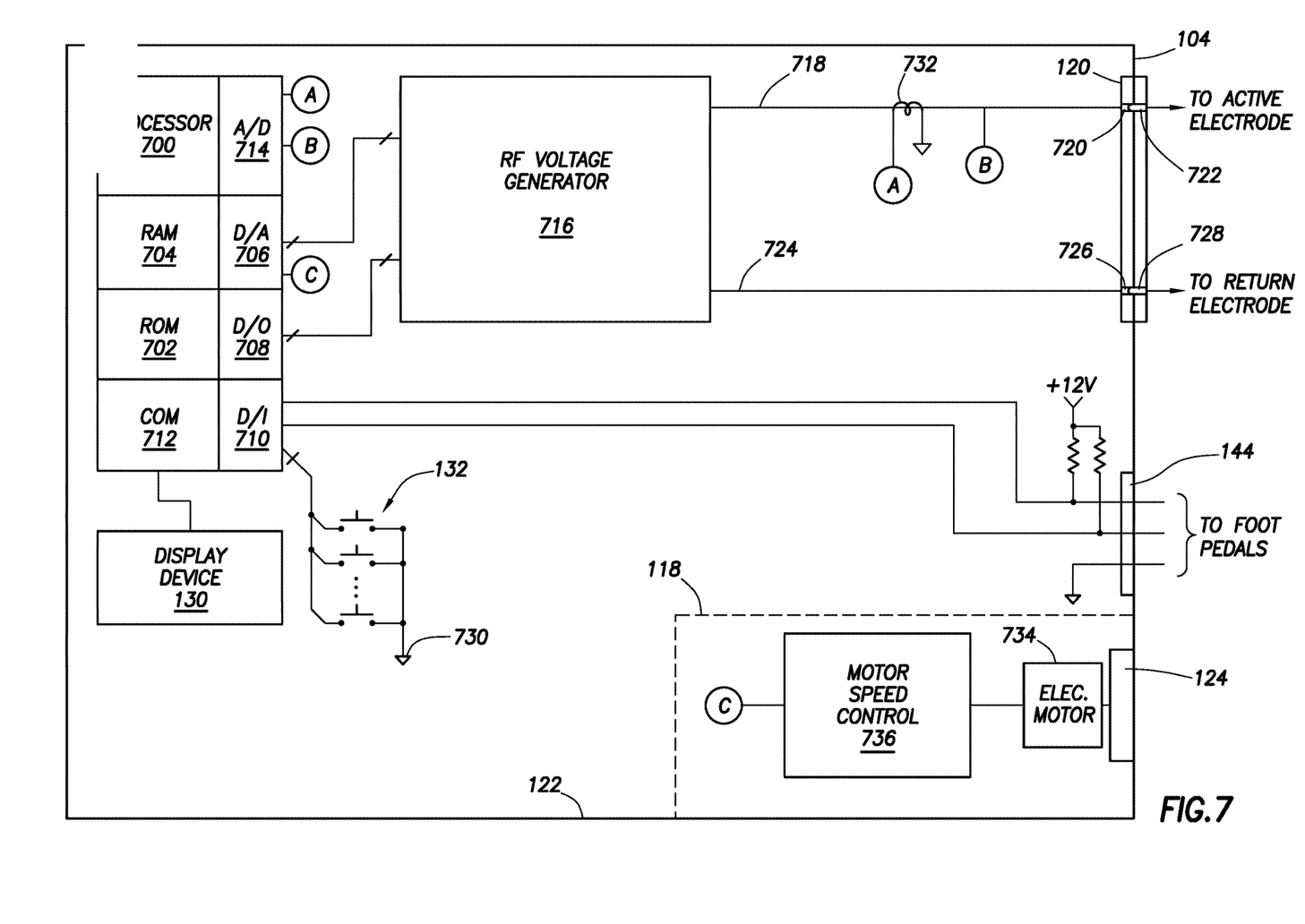
FIG. 7 shows an electrical block diagram of a controller in accordance with at least some embodiments.

FIG. 7 shows an electrical block diagram of a controller 104 in accordance with at least some embodiments. In particular, the controller 104 comprises a processor 700. The processor 700 may be a microcontroller, and therefore the microcontroller may be integral with read-only memory (ROM) 702, random access memory (RAM) 704, digital-to-analog converter (D/A) 706, analog-to-digital converter (A/D) 714, digital outputs (D/O) 708, and digital inputs (D/I) 710. The processor 700 may further provide one or more externally available peripheral buses, such as a serial bus (e.g., I²C), parallel bus, or other bus and corresponding communication mode. The processor 700 may further be integral with communication logic 712 to enable the processor 700 to communicate with external devices, as well as internal devices, such as display device 130. Although in some embodiments the processor 700 may be implemented in the form of a microcontroller, in other embodiments the processor 700 may be implemented as a standalone central processing unit in combination with individual RAM, ROM, communication, ND, D/A, D/O, and D/I devices, as well as communication hardware for communication to peripheral components.

ROM 702 stores instructions executable by the processor 700. In particular, the ROM 702 may comprise a software program that, when executed, causes the controller to control ablation, including in some cases increasing and decreasing peristaltic pump speed responsive to various feedback parameters. The RAM 704 may be the working memory for the processor 700, where data may be temporarily stored and from which instructions may be executed. Processor 700 couples to other devices within the controller 104 by way of the digital-to-analog converter 706 (e.g., in some embodiment the RF voltage generator 716), digital outputs 708 (e.g., in some embodiment the RF voltage generator 716), digital inputs 710 (e.g., interface devices such as push button switches 132 or foot pedal assembly 134 (FIG. 1)), and communication device 712 (e.g., display device 130).

Voltage generator 716 provides RF energy to create plasma. Voltage generator 716 generates an alternating current (AC) voltage signal that is coupled to active electrode (e.g. active electrode 202, 402, 606) of the wand 102. In some embodiments, the voltage generator 716 defines an active terminal 718 which couples to electrical pin 720 in the controller connector 120, electrical pin 722 the wand connector 114, and ultimately to the active electrode (e.g., active electrode 202, 402, 606). Likewise, the voltage generator defines a return terminal 724 which couples to electrical pin 726 in the controller connector 120, electrical pin 728 in the wand connector 114, and ultimately to a return electrode paired with the active electrode.

Additional active terminals and/or return terminals may be used. The active terminal 718 is the terminal upon which the voltages and electrical currents are induced by the voltage generator 716, and the return terminal 724 provides a return path for electrical currents. It would be possible for the return terminal 724 to provide a common or ground being the same as the common or ground within the balance of the controller 104 (e.g., the common 730 used on push-buttons 132), but in other embodiments the voltage generator 716 may be electrically "floated" from the balance of the controller 104, and thus the return terminal 724, when measured with respect to the common or earth ground (e.g., common 730) may show a voltage; however, an electrically floated voltage generator 716 and thus the potential for voltage readings on the return terminals 724 relative to earth ground does not negate the return terminal status of the terminal 724 relative to the active terminal 718.

The AC voltage signal generated and applied between the active terminal 718 and the return terminal 724 by the voltage generator 716 is RF energy. The voltage and current generated by voltage generators 716 may be delivered in a series of voltage pulses or AC voltage with a sufficiently high frequency such that the voltage is effectively applied continuously.

Still referring to FIG. 7, in some embodiment the controller 104 further comprises a mechanism to sense the electrical current provided to the active electrode. A sensing current provided to the active electrode may be by way of a current sense transformer 732. In particular, current sense transformer 732 may have a conductor of the active terminal 718 threaded through the transformer such that the active terminal 718 becomes a single turn primary. Current flow in the single turn primary induces corresponding voltages and/or currents in the secondary. Thus, the illustrative current sense transformer 732 is coupled to the analog-to-digital converter 714 (as shown by the bubble A). In some cases, the current sense transformer may couple directly to the analog-to-digital converter 714, and in other cases additional circuitry may be imposed between the current sense transformer 732 and the digital-to-analog converter 714, such as amplification circuits and protection circuits.

For example, in one example system the current sense transformer 732 is coupled to an integrated circuit device that takes the indication of current from the current sense transformer 732, calculates a root-mean-square (RMS) current value, and provides the RMS current values to the processor 700 through any suitable communication system (e.g., as an analog value applied the A/D 714, as a digital value applied to the multiple inputs of the D/I 710, as a packet message through the communication port 712). The current sense transformer is merely illustrative of any suitable mechanism to sense the current supplied to the active electrode, and other systems are possible. For example, a small resistor (e.g., 1 Ohm, 0.1 Ohm) may be placed in series with the active terminal 718, and the voltage drop induced across the resistor used as an indication of the electrical current.

Given that the voltage generator 716 is electrically floated, the mechanism to sense current is not limited to the just the active terminal 718. Thus, in yet still further embodiments, the mechanism to sense current may be implemented with respect to the return terminal 724. For example, illustrative current sense transformer 732 may be implemented on a conductor associated with the return terminal 724.

In some example systems, the feedback parameter used by the processor 700 regarding the voltage generator 716 is the electrical current flow. For example, in systems where the voltage generator 716 can accurately produce an output voltage independent of the impedance of the attached load, the processor 700 having set point control for the voltage created by the voltage generator 716 may be sufficient (e.g., to calculate a value indicative of impedance of the electrode circuit and plasma proximate the active electrode). However, in other cases, voltage too may be a feedback parameter. Thus, in some cases the active terminal 718 may be electrically coupled to the analog-to-digital converter 714 (as shown by bubble B). However, additional circuitry may be imposed between the active terminal 718 and the analog-to-digital converter 714, for example various step-down transformers, protection circuits, and circuits to account for the electrically floated nature of the voltage generator 716. In yet still other cases, voltage sense circuitry may measure the voltage, and the measured voltage values may be provided other than by analog signal, such as by way of packet-based communications over the communication port 712.

Still referring to FIG. 7 (and also FIG. 1), controller 104 in accordance with various embodiments further comprises the peristaltic pump 118. The peristaltic pump 118 may reside at least partially within the enclosure 122. The peristaltic pump comprises the rotor 124 mechanically coupled to a shaft of the electric motor 734. In some cases, and as illustrated, the rotor of the electric motor may couple directly to the rotor 124, but in other cases various gears, pulleys, and/or belts may reside between the electric motor 734 and the rotor 124. The electric motor 734 may take any suitable form, such as an AC motor, a DC motor, and/or a stepper-motor. To control speed of the shaft of the electric motor 734, and thus to control speed of the rotor 124 (and the volume flow rate at the wand) the electric motor 734 may be coupled to a motor speed control circuit 736. In the illustrative case of an AC motor, the motor speed control circuit 736 may control the voltage and frequency applied to the electric motor 734. In the case of a DC motor, the motor speed control circuit 736 may control the DC voltage applied to the electric motor 734. In the case of a stepper-motor, the motor speed control circuit 736 may control the current flowing to the poles of the motor, but the stepper-motor may have a sufficient number of poles, or is controlled in such a way, that the rotor 124 moves smoothly. Stated otherwise, the rotor 124 moves smoothly due to the high number of steps per turn.

The processor 700 couples to the motor speed control circuit 736, such as by way of the digital-to-analog converter 706 (as shown by bubble C). The processor 700 may be coupled in other ways as well, such as packet-based communication over the communication port 712. Thus, the processor 700, running a program, may read electrical current supplied on the active terminal 718, may read voltage supplied on the active terminal 718, and responsive thereto may make speed control changes (and thus volume flow rate changes) by sending speed commands to the motor speed control circuit 736. The motor speed control circuit 736, in turn, implements the speed control changes. Speed control changes may comprise changes in speed of the rotor 124 when desired, stopping the rotor 124 when desired, and in some modes of ablation temporarily reversing the rotor 124.

Figure 8:
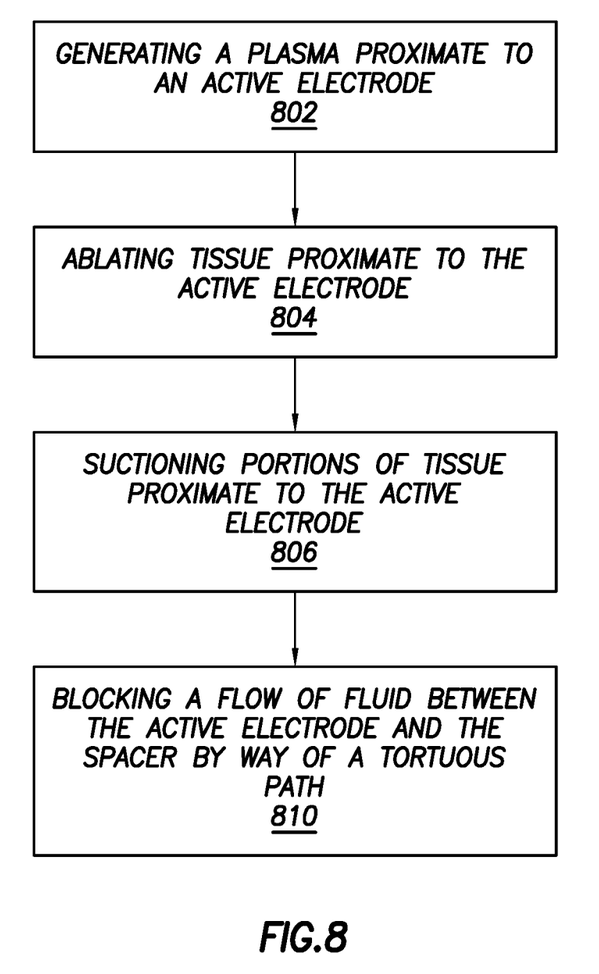
FIG. 8 shows a method in accordance with at least some embodiments.

FIG. 8 shows a method in accordance with at least some embodiments. In various embodiments, some of the blocks shown in FIG. 8 may be performed concurrently, in a different order than shown, or omitted. Additional method elements may be performed as desired.

At block 802, a plasma is generated proximate to an active electrode. The active electrode is disposed on the distal end of an elongate shaft of an electrosurgical wand. The active electrode mates with a spacer coupled on the distal end of the elongate shaft. At block 804 tissue is ablated proximate to the active electrode.

At block 806, portions of the fluid proximate to the active electrode are suctioned through a suction lumen defined within the elongate shaft. The suction lumen is fluidly connected to a suction channel defined within the spacer which is fluidly connected to apertures in the active electrode. At block 810 the flow of fluid may be blocked or reduced between the active electrode and the spacer. The flow of fluid may be blocked by way of a tortuous path between the active electrode and the suction channel of the spacer.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical wand comprising:
a handle that defines a proximal end of the electrosurgical wand;
an elongate shaft coupled to the handle, the elongate shaft defines a suction lumen therein;
a spacer coupled on a distal end of the elongate shaft, and the spacer is electrically insulative;
a distal surface defined by the spacer, the distal surface is flat and defines an outer edge of the spacer;
a suction channel through the spacer and fluidly coupled to the suction lumen, the suction channel defines an aperture at the distal surface;
an annular trough defined in the spacer, the annular trough comprises a closed bottom and an open top, the open top intersects the distal surface that is flat, and the annular trough fully encircles the suction channel;
an active electrode coupled to the distal surface of the spacer, wherein an outer edge of the active electrode aligns with the outer edge of the spacer; and
an annular wall that extends from the active electrode into the annular trough, and the annular wall encircles the suction channel of the spacer.

2. The electrosurgical wand of claim 1, wherein the annular wall fully encircles the suction channel of the spacer.

3. The electrosurgical wand of claim 1 further comprising an adhesive in the annular trough.

4. The electrosurgical wand of claim 1, wherein a height of the annular wall is nonzero and less than or equal to half of a width of the active electrode.

5. The electrosurgical wand of claim 1 further comprising no adhesive in the annular trough.

6. The electrosurgical wand of claim 1 wherein the outer edge of the active electrode is set back from the outer edge of the spacer by between 1 and 15 thousandths of an inch.

7. The electrosurgical wand of claim 1 wherein the outer edge of the active electrode does not overhang the outer edge of the spacer.

8. The electrosurgical wand of claim 1 wherein the active electrode further comprises an aperture aligned with the suction channel of the spacer.

* * * * *